(12) United States Patent
Shvartsburg et al.

(10) Patent No.: US 7,449,683 B2
(45) Date of Patent: Nov. 11, 2008

(54) METHOD AND APPARATUS FOR HIGH-ORDER DIFFERENTIAL MOBILITY SEPARATIONS

(75) Inventors: Alexandre A. Shvartsburg, Richland, WA (US); Richard D. Smith, Richland, WA (US); Gordon A. Anderson, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 472 days.

(21) Appl. No.: 11/237,523

(22) Filed: Sep. 28, 2005

(65) Prior Publication Data

US 2007/0069120 A1 Mar. 29, 2007

(51) Int. Cl.
*B01D 59/44* (2006.01)
(52) U.S. Cl. .................. 250/287; 250/281; 250/282
(58) Field of Classification Search .......... 250/281–300
See application file for complete search history.

(56) References Cited

U.S. PATENT DOCUMENTS

| | | | |
|---|---|---|---|
| 6,621,077 B1 | 9/2003 | Guevremont et al. | |
| 6,639,212 B1 | 10/2003 | Guevremont et al. | |
| 6,690,004 B2 * | 2/2004 | Miller et al. | 250/286 |
| 6,703,609 B2 | 3/2004 | Guevremont et al. | |
| 6,713,758 B2 | 3/2004 | Guevremont et al. | |
| 6,770,875 B1 | 8/2004 | Guevremont et al. | |
| 6,806,463 B2 | 10/2004 | Miller et al. | |
| 6,815,668 B2 | 11/2004 | Miller et al. | |
| 6,822,224 B2 | 11/2004 | Guevremont et al. | |
| 6,972,407 B2 * | 12/2005 | Miller et al. | 250/287 |
| 7,075,068 B2 * | 7/2006 | Miller et al. | 250/290 |
| 7,078,678 B2 * | 7/2006 | Potvin et al. | 250/286 |
| 7,084,394 B2 * | 8/2006 | Guevremont et al. | 250/286 |
| 7,157,701 B2 * | 1/2007 | Ermer | 250/287 |
| 7,285,774 B2 * | 10/2007 | Guevremont | 250/290 |
| 7,381,944 B2 * | 6/2008 | Cameron et al. | 250/282 |

(Continued)

OTHER PUBLICATIONS

Mason, E.A.; McDaniel, E.W. Transport Properties of Ions in Gases, Wiley, New York, 1988.

(Continued)

*Primary Examiner*—Jack I Berman
*Assistant Examiner*—Andrew Smyth
(74) *Attorney, Agent, or Firm*—James D. Matheson

(57) ABSTRACT

The present invention relates generally to separation of ions based on their transport properties. More particularly, the invention relates to separation of ionic mixtures and characterization of ions in gases using higher-order differential ion mobility spectrometry (HODIMS) enabled by asymmetric waveforms of fundamentally new types. The invention discloses a method and apparatus for separation of ionic mixtures and characterization, identification, or quantification of ions in a gas based substantially on the terms of third or higher order in a series expansion of ion mobility as a function of electric field intensity. This is achieved using a periodic, time-dependent electric field with novel waveform profiles that cancel or substantially reduce the contributions to time-averaged ion motion of the leading n (where $n \geq 2$) terms of that expansion, thereby achieving ion separations based substantially on the (n+1)th term. Separations using HODIMS with different n are expected to be highly orthogonal, enabling multidimensional separations employing HODIMS analyzers of different orders. The expected high orthogonality between HODIMS and mass spectrometry or ion mobility spectrometry would make HODIMS/MS and HODIMS/IMS combinations powerful analytical tools of broad utility.

50 Claims, 8 Drawing Sheets

U.S. PATENT DOCUMENTS

| | | | |
|---|---|---|---|
| 2003/0146377 A1* | 8/2003 | Miller et al. | 250/286 |
| 2004/0124350 A1* | 7/2004 | Miller et al. | 250/286 |
| 2005/0012037 A1* | 1/2005 | McCracken | 250/286 |
| 2005/0040330 A1 | 2/2005 | Kaufman | |
| 2005/0145789 A1* | 7/2005 | Miller et al. | 250/290 |
| 2005/0253061 A1* | 11/2005 | Cameron et al. | 250/287 |
| 2005/0269500 A1* | 12/2005 | Potvin et al. | 250/281 |
| 2006/0038119 A1* | 2/2006 | Guevremont et al. | 250/282 |
| 2006/0038121 A1* | 2/2006 | Guevremont | 250/290 |

OTHER PUBLICATIONS

Lubman, D.M. Anal. Chem. 1984, 56, 1298.

Hill, H.H.; Siems, W.F.; St. Louis, R.H.; McMinn, D.G. Anal. Chem. 1990, 62, A1201.

von Helden, G.; Wyttenbach, T.; Bowers, M.T. Science 1995, 267, 1483.

Clemmer, D.E.; Hudgins, R.R.; Jarrold, M.F. J. Am. Chem. Soc. 1995, 117, 10141.

Hoaglund, C.S.; Valentine, S.J.; Sporleder, C.R.; Reilly, J.P.; Clemmer, D.E. Anal. Chem. 1998, 70, 2236.

Shvartsburg, A.A.; Hudgins, R.R.; Dugourd, P.; Jarrold, M.F. Chem. Soc. Rev. 2001, 30, 26.

Ruotolo, B.T.; Gillig, K.J.; Woods, A.S.; Egan, T.F.; Ugarov, M.V.; Schultz, J.A.; Russell, D.H. Anal. Chem. 2004, 76, 6727.

Shvartsburg, A.A.; Schatz, G.C.; Jarrold, M.F. J. Chem. Phys. 1998, 108, 2416.

Tang, K.; Shvartsburg, A.A.; Lee, H.N.; Prior, D.C.; Buschbach, M.A.; Li, F.; Tolmachev, A.V.; Anderson, G.A.; Smith, R.D. Anal. Chem. 2005, 77, 3330.

Buryakov, I.A.; Krylov, E.V.; Nazarov, E.G.; Rasulev, U.K. Int. J. Mass Spectrom. Ion Proc. 1993, 128, 143.

Eiceman, G.A.; Tadjikov, B.; Krylov, E.; Nazarov, E.G.; Miller, R.A.; Westbrook, J.; Funk, P. J. Chromatogr. A 2001, 917, 205.

Miller, R.A.; Nazarov, E.G.; Eiceman, G.A.; King, A.T. Sens. Actuat. A 2001, 91, 301.

Buryakov, I.A. J. Chromatogr. B 2004, 800, 75.

Barnett, D.A; Purves, R.W.; Guevremont, R. Nucl. Instrum. Meth. Phys. Res. A 2000, 450, 179.

Purves, R.W.; Guevremont, R.; Day, S.; Pipich, C.W.; Matyjaszczyk, M.S. Rev. Sci. Instrum. 1998, 69, 4094.

Guevremont, R.; Purves, R.W. Rev. Sci. Instrum. 1999, 70, 1370.

Guevremont, R. J. Chromatogr. A 2004, 1058, 3.

Shvartsburg, A.A.; Tang, K.; Smith, R.D. J. Am. Soc. Mass Spectrom. 2004, 15, 1487.

Shvartsburg, A.A.; Tang, K.; Smith, R.D. J. Am. Soc. Mass Spectrom. 2005, 16, 2.

Shvartsburg, A.A.; Tang, K.; Smith, R.D. Anal. Chem. 2004, 76, 7366.

Guevremont, R.; Ding, L.; Ells, B.; Barnett, D.A.; Purves, R.W. J. Am. Soc. Mass Spectrom. 2001, 12, 1320.

Venne, K.; Bonneil, E.; Eng, K.; Thibault, P. Anal. Chem. 2005, 77, 2176.

Borysik, A.J. H.; Read, P.; Little, D.R.; Bateman, R.H.; Radford, S.E.; Ashcroft, A.E., Rapid Commun. Mass Spectrom. 2004, 18, 2229.

Robinson, E.W.; Williams, E.R. J. Am. Soc. Mass Spectrom. 2005, 16, 1427.

Tang, K.; Li, F.; Shvartsburg, A.A.; Strittmatter, E.F.; Smith, R.D. Anal. Chem. 2005, 77, 6381.

PCT International Search Report and Written Opinion of the International Searching Authority (Jan. 16, 2006).

Shvartburg, et al., Journal of Amer. Society for Mass Spec, vol. 16, No. 9, Sep. 2005, pp. 1447-1455.

Shvartburg, et al., J. Am. Soc. Mass Spectrom, Jan. 2005, vol. 16, No. 1, pp. 2-12, XP002413005.

Guevremont et al., Journal of Chromatography, vol. 1058, No. 1-2, Nov. 2004, pp. 3-19, XP004638461.

Shvartsburg, et al., J. Phys Chem A, vol. 110, No. 8, Mar. 2, 2006, pp. 2663-2673, XP002413006.

* cited by examiner

METHOD AND APPARATUS FOR HIGH-ORDER DIFFERENTIAL MOBILITY SEPARATIONS

FIELD OF THE INVENTION

The present invention relates generally to separation of ions based on their transport properties. More particularly, the invention relates to separation of ionic mixtures and characterization of ions in gases using higher-order differential ion mobility spectrometry enabled by asymmetric waveforms of a new type.

BACKGROUND OF THE INVENTION

Separation of ionic mixtures and characterization of ions in the gas phase using ion mobility techniques has become common in analytical chemistry. The key advantage of gas-phase separations over condensed-phase methods is exceptional speed allowed by rapid molecular motion in gases. Since their first demonstration a decade ago, instrumental platforms combining ESI or MALDI soft-ionization sources, ion mobility separations, and mass-spectrometry (MS) have undergone a sustained development that has improved their resolution and sensitivity to the levels demanded by practical applications. Commercial introduction of such systems is accelerating the adoption of combined ion mobility/mass spectrometry (MS) as a mainstream analytical paradigm, in particular for complex biological samples such as proteolytic digests and mixtures of lipids, nucleotides, or metabolites.

Ion mobility spectrometry (IMS) has been known since the 1970's. In IMS, ions drift through a non-reactive buffer gas under the influence of a modest electric field, wherein the drift velocity (v) in the field having intensity E is determined by a quantity known as ion mobility (K) according to equation [1]:

$$v = K(E) \quad [1]$$

Measured mobilities are normally converted to reduced values ($K_0$) by adjusting the buffer gas temperature (T, Kelvin) and pressure (P, Torr) to standard (STP) conditions, via equation [2]:

$$K_0 = K(P/760) \times (273.15/T) \quad [2]$$

The mobility of an ion always depends on the electric field and may be expressed as an infinite series of even powers over (E/N), where N is the gas number density, by the series expansion of equation [3]:

$$K(E/N) = K(0)[1 + a(E/N)^2 + b(E/N)^4 + c(E/N)^6 + d(E/N)^8 + \ldots a_j(E/N)^{2j}] \quad [3]$$

IMS measures K(E/N) at a particular E/N. However, over an experimentally relevant range of E/N, e.g., from 0 to ~100 Td, K(E/N) varies by a few percent at most, except for some monatomic and other small ions. Thus, though K(E/N) could be revealed by high-field IMS measurements at low pressure P, in practice, IMS separates ion mixtures by zero-field mobility K(0). Separation, characterization, or identification of ions is based on coefficients with the terms of the series expansion: $a_j$. The mobility of an ion is related to its size and mass m, especially within classes of homologous or chemically/structurally similar species. The correlation between ion mobility and mass means a limited orthogonality between IMS and MS analyses. For example, ions of the same charge state z follow certain trend lines in 2-D IMS/MS plots depending on chemical composition and compound type. Trend lines are described in the art for atomic nanoclusters (including carbon, semiconductor, and metal species) and biomolecules (including peptides, lipids, and nucleotides). In ESI, complex biological analytes such as tryptic digests generally yield ions with a distribution of "z" that have different trend lines in IMS/MS space. While this improves the orthogonality between IMS and MS and thus increases the 2-D IMS/MS peak capacity, the correlation between ion mobility and mass remains a fundamental limitation of IMS/MS methodology.

Field asymmetric waveform ion mobility spectrometry (FAIMS) is another method to separate ions based on their transport properties in gases. FAIMS separation is based not on the absolute mobility, but the difference between K at high and low E. A FAIMS separation may be achieved by a periodic time-dependent electric field E(t) that meets the conditions of equation [4] with respect to integrals over period $\Delta t$:

$$\int E(t)dt = 0; \int E^3(t)dt \neq 0 \quad [4]$$

An E(t) subject to condition [4] cancels the effect on ion motion provided by the first but not higher terms of polynomial [3]. The higher terms result in a net motion of ions through gas with mean velocity equal to $$\langle v \rangle = \left( \int_{t_0}^{t_0+\Delta t} K(E)E(t)dt \right) / \Delta t \quad [5]$$

which for K(E), given by equation [4], expands into equation [6]:

$$\langle v \rangle = K(0) \times [\int E(t)dt + (a/N^2)\int E^3(t)dt + (b/N^4)\int E^5(t)dt + (c/N^6)\int E^7(t)dt + (d/N^8)\int E^9(t)dt + (e/N^{10})\int E^{11}(t)dt]/\Delta t \quad [6]$$

The motion may be offset by a drift with velocity $v_C$ due to constant "compensation field" $E_C$ defined by equation [7]:

$$v_C \approx E_C \times K(0) \quad [7]$$

with $E_C$ dependent on the ion and the buffer gas and calculated via equation [8]:

$$E_C \approx [(a/N^2)\int E^3(t)dt + (b/N^4)\int E^5(t)dt + (c/N^6)\int E^7(t)dt + (d/N^8)\int E^9(t)dt + (e/N^{10})\int (E^{11})(t)dt + \ldots]/\Delta t, \quad [8]$$

By equation [8], independence of $E_C$ of K(0) allows FAIMS to disperse ions by the sum of the second and further terms of equation [3] regardless of the absolute mobility. At a sufficiently low peak amplitude of E(t), known as the "dispersion field" ($E_D$), $E_C$ is mostly determined by a, the coefficient with the leading term of equation [8]. Subsequent terms (especially the $2^{nd}$ term) affect the FAIMS response at higher $E_D$, which in some cases allows measuring the coefficient b. Still, FAIMS separations are primarily controlled by the value of a, and differences between further coefficients do no create a significant orthogonality and so are of little analytical utility.

The condition in equation [4] may be satisfied by an infinite number of E(t) functions. However, FAIMS performance is optimized by maximizing $\langle v \rangle \propto \int E^3(t)dt/\Delta t$ (ignoring higher-order terms in equation [6]). This condition is ideally achieved by a "rectangular" waveform, where E(t) switches between segments of "high field" ($E_D$) applied over a time $t_D$ and low field ($E_L$) in the opposite direction applied over a time $t_L$. The criterion $\int E(t)dt = 0$ of condition [4] requires $E_D/E_L = -t_L/t_D$. That quantity (known as the "high-to-low" ratio f) may mathematically vary between 1 and $+\infty$, but the best FAIMS performance is provided by f=2, producing equation [9]:

$$E(t)=E_D\{t\epsilon[0;\ t/3]\};\ E(t)=-E_D/2\{t\epsilon[\Delta t/3;\ \Delta t]\}, \quad [9]$$

with $<v>$ and $E_C$ defined by equations [10] and [11]:

$$<v>=K(0)[(a/N^2)E_D^3/4+5(b/N^4)E_D^5/16+\overline{o}(cE_D^7/N^6)]/\Delta t \quad [10]$$

$$E_C=[(a/N^2)E_D^3/4+5(b/N^4)E_D^5/16+\overline{o}(cE_D^7/N^6)]/\Delta t \quad [11]$$

Waveforms defined by equation [9] and corresponding model ion trajectories are plotted in FIG. 1a and, for the inverted E(t) polarity, in FIG. 1b. Calculations do not account for ion diffusion or space-charge effects, which is proper for the purpose of comparing trajectories induced by different E(t). The E(t) form influences the diffusion only slightly through high-field and anisotropic terms and does not affect Coulomb repulsion. Commercial FAIMS analyzers use not the ideal E(t) of equation [9], but its approximation, by either a bisinusoidal (a sum of two harmonics) or a clipped, displaced sinusoidal waveform. Substitution of these waveforms for the rectangular E(t) sacrifices some resolution and/or sensitivity but simplifies engineering substantially.

In practice, FAIMS analyses involve pulling an ion beam through a gap between two electrodes (the so-called "analytical gap") by a gas flow or weak electric field along the gap. A voltage waveform applied to this electrode pair creates the field $[E(t)+E_C]$ across the gap. Parallel planar, coaxial cylindrical, and concentric spherical electrode geometries (and their combinations) are known in the art. At any given $E_C$, ideally only one species with K(E) yielding $<v>=v_C$ is balanced in the gap and may pass. Other ions drift across the gap and are eventually neutralized on an electrode. A spectrum of an ionic mixture may be produced by scanning $E_C$.

Equation [3] indicates that a differential IMS effect (for any n) should, in principle, exist at any E. However, the FAIMS resolution depends on $<v>$ that scales with $E_D^3$ by equation [10], and in practice, separation becomes useful at $E_D/N$ ~40-50 Td, with optimum performance achieved at ~65-80 Td.

Fundamentally, the value of "a" is not related to m as closely as K(0). In particular, "a" may be both positive and negative, while K is always positive. Hence FAIMS is, in general, more orthogonal to MS than IMS. That deduction has broad experimental support, e.g., for tryptic peptide ions, FAIMS and MS separations are virtually independent, but IMS and MS are substantially correlated. This is a major advantage of FAIMS/MS over IMS/MS.

A successful development of FAIMS prompts the question whether further conceptually new separation approaches based on ion transport in gases might exist. To be useful, those approaches must exhibit a substantial orthogonality to both FAIMS and IMS or outperform them in other respects. There remains a need for novel separation approaches and devices providing high resolution and sensitivity, and significant orthogonality to known IMS and FAIMS separations, as well as to MS.

SUMMARY OF THE INVENTION

In its broadest aspects, the invention provides for a method and apparatus for separation of ionic mixtures and characterization, identification, or quantification of ions in a gas based substantially on the terms of K(E) series expansion that have the order higher than at least the quadratic term over (E/N), referred to below as higher-order differential ion mobility separations (HODIMS). This is achieved using a periodic, time-dependent electric field with novel waveform profiles that cancel or substantially reduce the contributions to time-averaged ion motion of the leading n (where $n \geq 2$) terms of that expansion, enabling separations based substantially on coefficients with the $(n+1)^{th}$ and subsequent terms. With respect to K(E) defined by equation [3], this would mean separations based on the terms with coefficients b and higher, or c and higher, or d and higher, etc., while the contributions of at least the linear term (determined in IMS) and $2^{nd}$ term with coefficient a (determined in FAIMS) are substantially eliminated.

In an embodiment of the invention, the periodic time-dependent electric field satisfies, over the period, the condition $\{\int E(t)=\int E^3(t)=0;\ \int E^5(t)\neq 0\}$, canceling the contributions to time-averaged ion motion of the terms of K(E) expansion that are independent of E and proportional to $E^2$.

In another embodiment, the condition satisfied is $\{\int E(t)=\int E^3(t)=\int E^5(t)=0;\ \int E^7(t)\neq 0\}$, canceling the contributions of the terms that are independent of E and proportional to $E^2$ or $E^4$.

In yet another embodiment, the condition satisfied is $\{\int E(t)=\int E^3(t)=\int E^5(t)=\int E^7(t)=0;\ \int E^9(t)\neq 0\}$, canceling the contributions of the terms that are independent of E and proportional to $E^2$, $E^4$, or $E^6$.

In yet another embodiment, the analytical gap is contained between at least two electrodes, and the electric field $[E(t)+E_C]$ therebetween is produced by at least one voltage waveform applied to at least one electrode. In particular, the total electric field may be produced by voltages applied to at least two electrodes.

In another embodiment, the electrodes have a parallel planar geometry establishing a spatially homogeneous electric field. Alternatively, at least one electrode may have a curved geometry (including but not limited to cylindrical, conical, spherical, hemispherical, ellipsoidal, ovoid, and combinations thereof), establishing an inhomogeneous electric field. In particular, the gap geometry may be selected from the group of two coaxial cylinders, two concentric spheres or hemispheres, and combinations thereof. When the waveform polarity is chosen to form a pseudopotential well inside the analytical gap, a plurality of ions may be focused or confined within the gap. In particular, this confinement may be used to guide ions through the analytical gap to a desired volume in space and/or to trap ions in such a volume for storage or accumulation.

In still yet another embodiment, the temperature of at least one electrode may be controlled. In particular, the temperatures of at least two of the electrodes may differ providing a temperature gradient across the analytical gap that renders the value of N and thus of E/N across the analytical gap spatially inhomogeneous, creating a pseudopotential well. This well may likewise be used to guide or trap ions inside the analytical gap.

In other embodiments, ions may be moved through the analytical gap by a gas flow that may be heated or cooled prior to inflow into the gap. Alternatively, ions may be moved by a secondary electric field orthogonal to E(t) and $E_C$, or combination thereof with gas flow. In particular, the secondary field may be produced using segmented electrodes and may be either constant or time-dependent. In other embodiments, the buffer gas in the analytical gap may be a pure gas or vapor. It also may be a mixture of at least two homomolecular gases or vapors. In particular, such mixtures may have a composition that, at a sufficiently high electric field, results in substantial deviations from Blanc's law for ion mobilities. Also, in particular, the gas may comprise a gas-phase insulator that raises the electrical breakdown threshold. In one embodiment, the gas pressure in the analytical gap exceeds that in a preceding region from which the ions enter the gap, such that the gas flows out of the analytical gap in a direction opposite to that of ion ingress. In other embodiments, ions may also be introduced into the analytical gap continuously. Alternatively, ions may be injected into the gap in discrete pulses. In particular, the time of their passage through the gap may be monitored, and, when ions are moved through the gap by secondary electric field, an IMS separation may be effected simultaneously with HODIMS filtering.

In other embodiments, at least a portion of the ions may be dissociated during, at the end of, or after the HODIMS separation.

In other embodiments, the method may be sequentially coupled to one or more iterations of the method having different values for the parameter n. In another embodiment, the method is sequentially coupled on- or off-line to at least one additional analytical method including, but not limited to, ion mobility spectrometry, field asymmetric waveform ion mobility spectrometry, mass spectrometry, gas chromatography, photoelectron spectroscopy, photodissociation spectroscopy, liquid chromatography, supercritical fluid chromatography, capillary electrophoresis, capillary isoelectric focusing, gel separations in one or more dimensions, and combinations thereof.

In other embodiments, the periodic field E(t) may comprise a series of distinct discrete field settings or a superposition of harmonics, or a combination thereof. The discrete settings may, for example, be generated by plurality of operably connected switched power sources, each providing at least one voltage setting. A superposition of harmonics may, for example, be produced by a plurality of operably connected oscillating circuits, each providing at least one periodic waveform.

In yet another embodiment, the waveform-generating device may produce a sub-scale form of E(t), amplified to the desired dispersion voltage by, e.g., a transformer.

DETAILED DESCRIPTION

Figure 1:
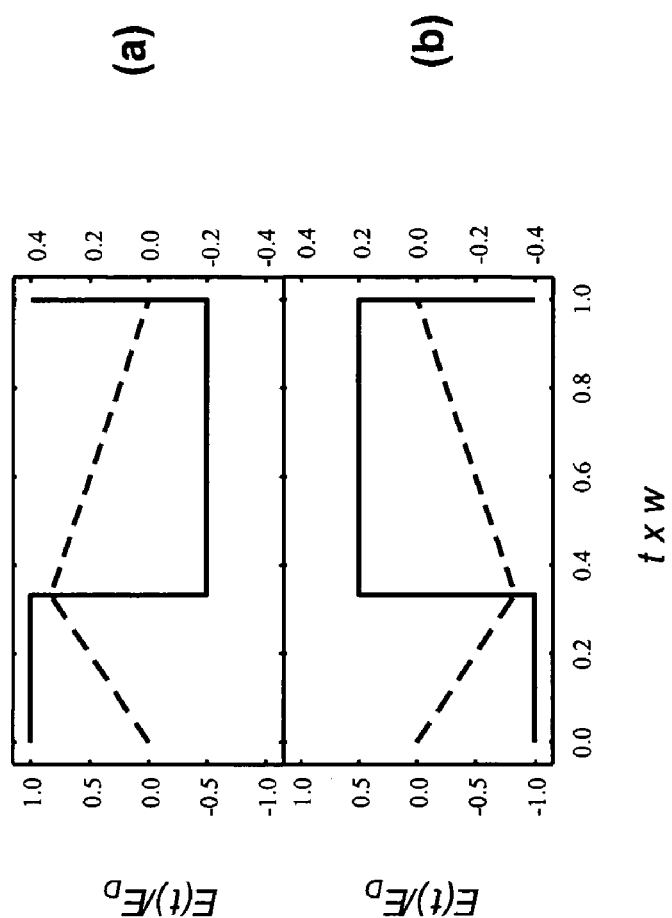
FIGS. 1a-1b (prior art) illustrate two possible polarities for a period of an optimum FAIMS waveform E(t) (solid lines) and model trajectories for ions experiencing a period of [E(t)+ $E_C$] (dashed lines).

While the present disclosure is exemplified by specific embodiments, it should be understood that the invention is not limited thereto, and variations in form and detail may be made without departing from the spirit and scope of the invention. All such modifications as would be envisioned by those of skill in the art are hereby incorporated.

Feasibility of Higher-Order Differential Ion Mobility Separations

In principle, there are an infinite number of distinct differential ion mobility separations based on the $3^{rd}$ and higher terms of K(E) expansion in equation [3] just as IMS and FAIMS are based on the $1^{st}$ and $2^{nd}$ terms, respectively. First, we prove the physical possibility of separations based on the terms of equation [3] beyond an arbitrarily chosen order using E(t) comprising a number (k) of discrete field settings $\{E_1, \ldots, E_k\}$ applied over finite time periods $\{t_1, \ldots, t_k\}$. For mathematical simplicity, all E and t values are scaled in terms of, respectively, $E_1$ and $t_1$. For separations based on the $b(E/N)^4$ and higher terms of equation [3], the E(t) must satisfy the following system denoted in [12]:

$$\int E(t)dt=0; \quad \int E^3(t)dt=0; \quad \int E^5(t)dt \neq 0 \quad [12]$$

This can not be achieved using a "rectangular" (k=2) waveform (known in the FAIMS art) with any f value. Indeed, the equations in system [12] reduce to $(f^3-f=0)$ with roots f={0; 1} where the waveform does not exist and f=−1 where it is symmetric, and $\int E^{2n-1}(t)dt=0$ for any n. However, an E(t) comprising 3 different settings can satisfy the condition denoted in [12]. The system [12] contains 2 equations but 4 variables $\{t_2; E_2; t_3; E_3\}$, hence an infinite number of such waveforms exist. An optimum E(t) would maximize $\int E^5(t) dt/\Delta t$, which, through manipulation of equations in [12], may be derived as equation [13]:

$$\int E^5(t)dt/\Delta t = \frac{1+t_2 E_2^5 - [(1+t_2 E_2^3)^2/(1+t_2 E_2)]}{1+t_2+\sqrt{(1+t_2 E_2)^3/(1+t_2 E_2^3)}} \quad [13]$$

By numerical optimization, function [13] maximizes at $\{t_2=2; \; E_2=(\sqrt{5}-1)/4 \approx 0.309; \; t_3=2; \; E_3=-(1+\sqrt{5})/4 \approx -0.809\}$. Since the order of $t_2$ and $t_3$ is not constrained, this solution yields two waveforms that are mirror images with respect to the time axis inversion, with E(t) given by equations [14] and [14]':

$$E(t)=E_D\{t\epsilon[0; \Delta t/5]\}; E_2 E_D\{t\epsilon[\Delta t/5; 3\Delta t/5]\}; E_3 \; E_D \{t\epsilon[3\Delta t/5; \Delta t]\}; \quad [14]$$

$$E(t)=E_D\{t\epsilon[0; \Delta t/5]\}; E_3 E_D\{t\epsilon[\Delta t/5; 3\Delta t/5]\}; E_2 E_D\{t\epsilon [3\Delta t/5; \Delta t]\}; \quad [14']$$

Figure 2:
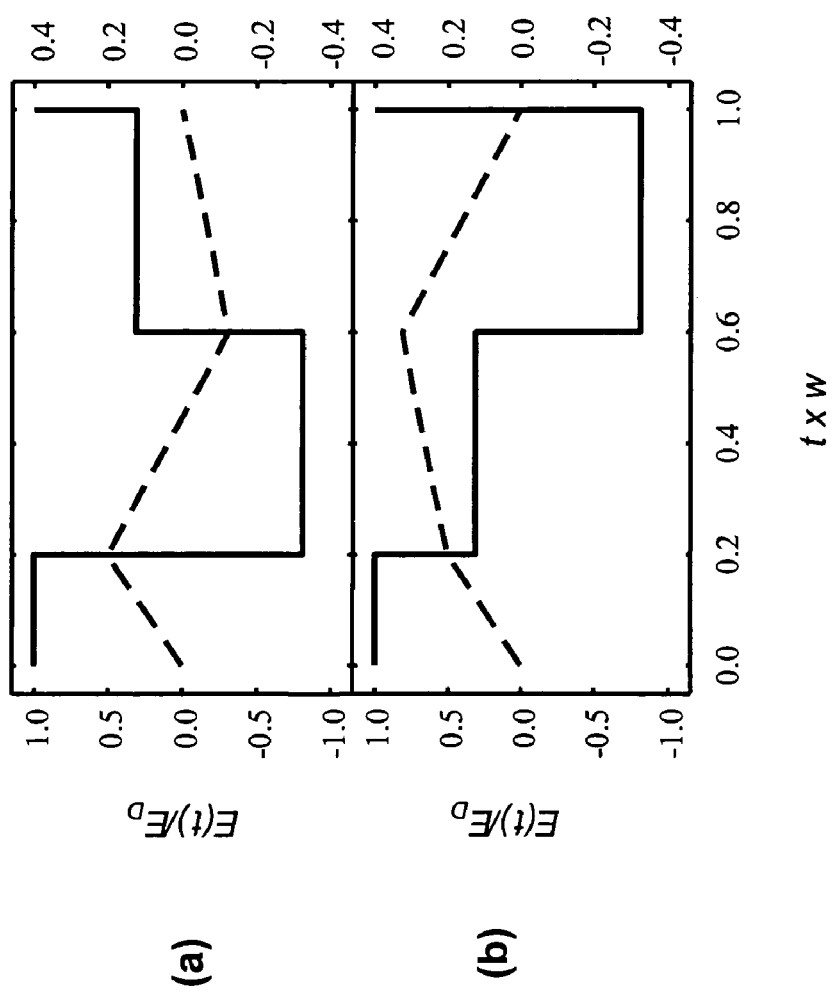
FIGS. 2a-2b illustrate mirror images for E(t) with respect to time axis inversion for a period of the optimum E(t) for $3^{rd}$ order ion mobility separations (solid lines) and corresponding ion trajectories (dashed lines).
Figure 3:
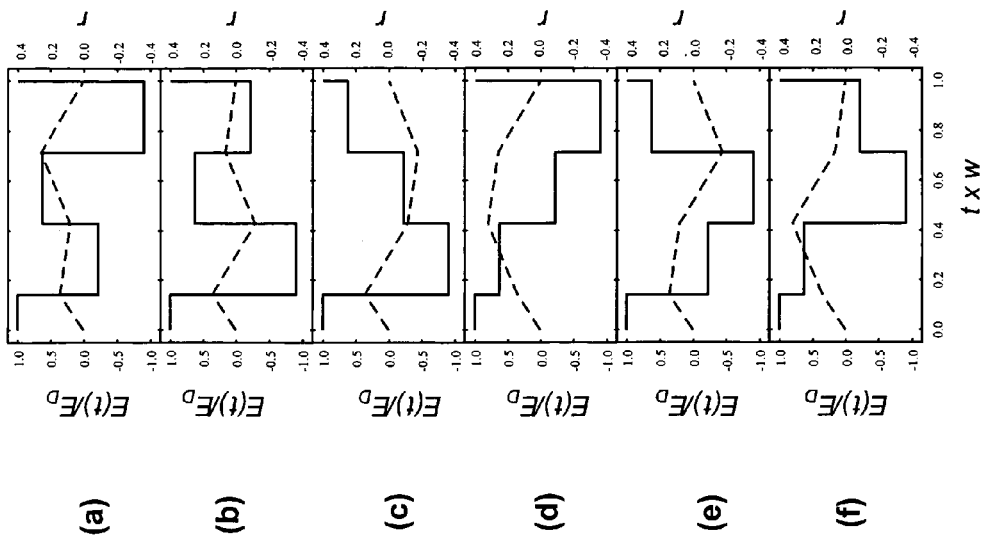
FIGS. 3a-3f illustrate three optimum E(t) (over a period) for $4^{th}$ order ion mobility separations with their mirror images with respect to time axis inversion (solid lines) and corresponding ion trajectories (dashed lines).
Figure 4:
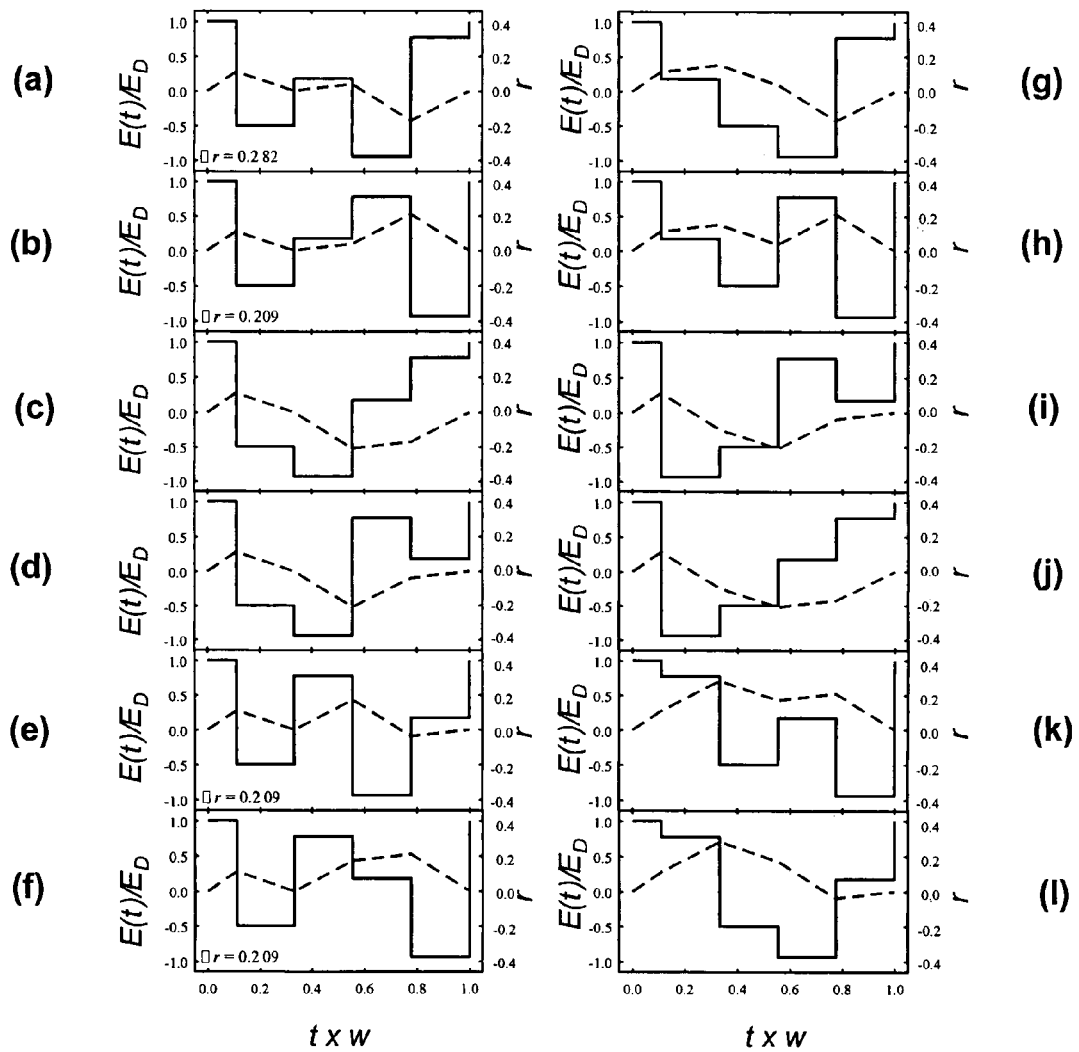
FIGS. 4a-4l illustrate the optimum E(t) for $5^{th}$ order separations. Each waveform shown has a corresponding mirror image (not shown) with respect to the time axis inversion.

The waveforms of equations [14] and [14'] are illustrated in FIG. 2a and FIG. 2b, respectively. The polarities of both waveforms may also be inverted. The maximum of equation [13] is $1/16$, yielding equations [15] and [16]:

$$<v>=K(0)[(b/N^4)E_D^5/16+\overline{o}(cE_D^7/N^6)]/\Delta t \quad [15]$$

$$E_C=[(b/N^4)E_D^5/16+\overline{o}(cE_D^7/N^6)]/\Delta t \quad [16]$$

In equation [16], $E_C$ is independent of both $K(0)$ and the coefficient "a". This essentially is the $3^{rd}$-order ion mobility separation, primarily by the value of "b". The waveforms of equations [14] and [14'] also yield non-zero higher-order terms in equation [6] involving coefficients $\{c, d, \ldots\}$ that influence the results, especially at higher $E_D$ where the $\overline{o}(cE_D^7/N^6)$ term grows in importance.

The waveforms in FIG. 2a and FIG. 2b are not equivalent as ion trajectories in the field of $[E(t)+E_C]$ over the period differ even though the final displacements are null in both cases. Yet, maximum amplitudes of ion oscillation during the period $(\Delta r)$ are equal. The $(\Delta r)$ parameter determines the "tightness" of a given gap width and thus is critical in the design of HODIMS experiments, as discussed below. The $(\Delta r)$ parameter is given by equation [17]:

$$\Delta r = C_E K(E) E_D / w \quad [17]$$

where $C_E$ is a numerical factor ($0 < C_E < 1$) depending on the $E(t)$ profile. For equations [14] and [14'], $C_E \approx 0.3236$, i.e., slightly lower than $C_E = 1/3$ in FAIMS.

The approach described herein can be used to design $E(t)$ for separations of still higher orders. For the $4^{th}$-order separation (primarily by the value of coefficient "c"), a waveform must meet the condition denoted in [18]:

$$\int E(t)dt=0; \int E^3(t)dt=0; \int E^5(t)dt=0; \int E^7(t)dt\neq 0 \quad [18]$$

Setting equation [13] to zero yields only the solutions that cancel each $\int E^{2n+1}(t)dt$ term, so no waveform with $k \leq 3$ can satisfy the system [18]. Seeking an $E(t)$ with $k=4$ provides 6 variables $\{t_2; E_2; t_3; E_3; t_4; E_4\}$ to satisfy 3 equations in [18]. Again, that can be achieved by an infinite multiplicity of $E(t)$, but in this case the number of variables has prevented an a priori optimization. However, the 1:2 optimum ratio of $t_1:t_2$ for $n=2$ (in FAIMS) and the 1:2:2 ratio of $t_1:t_2:t_3$ for $n=3$ appear to reveal a rule extrapolating to the 1:2:2:2 ratio for $t_1:t_2:t_3:t_4$ for $n=4$. While we cannot rigorously prove that recipe for maximizing $\int E^7(t)dt$, the results below support its verity. The constraint leaves 3 variables $\{E_2; E_3; E_4\}$ for 3 equations in [18], defining a unique solution obtained numerically as $\{-0.223; 0.623; -0.901\}$. Since $t_2=t_3=t_4$, which value is assigned to which of $E_2$, $E_3$, and $E_4$ is immaterial. By combinatorial rules, this allows $(n-1)!=6$ different $E(t)$ with two polarities each, making three pairs of $E(t)$ that are identical with respect to the time axis inversion as illustrated in FIGS. 3a and 3b, FIGS. 3c and 3d, and FIGS. 3e and 3f, respectively. Any of these requires $E_C$ given by equation [19]:

$$E_C=[(c/N^6)E_D^7/64+\overline{o}(dE_D^9/N^8)]/\Delta t \quad [19]$$

where ion separation is independent of $K(0)$, a, and b. Equations [11], [16], and [19] show the integer coefficient with leading term decreasing by a factor of 4 at each higher n: $1/4$ for $n=2$, $1/16$ for $n=3$, and $1/64$ for $n=4$. This trend supports the postulate of 1:2:2:2 ratio for waveform segment durations. The six ideal $E(t)$ are not equivalent and produce different ion trajectories (FIGS. 3a-3f). Unlike for $n=3$, those have different $\Delta r$ ($C_E \approx 0.257$ for a, b; $C_E \approx 0.321$ for c-e), which would result in a different instrumental response.

For the $5^{th}$-order separation by the value of coefficient d, $E(t)$ must satisfy the system [20]:

$$\int E(t)dt=0; \int E^3(t)dt=0; \int E^5(t)dt=0; \int E^7(t)dt=0; \int E^9(t)dt\neq 0 \quad [20]$$

This condition can be met by an infinite number of waveforms with $k \geq 5$. Assuming $t_1:t_2:t_3:t_4:t_5=1:2:2:2:2$ by the above-formulated rule, a numerical optimization of four variables $\{E_2; E_3; E_4; E_5\}$ for maximum $\int E^9(t)dt$ yields $\{0.174; -0.500; 0.770; -0.940\}$. Again, as $t_2=t_3=t_4=t_5$, those values may be freely permuted within the $\{E_2; E_3; E_4; E_5\}$ set, creating $(n-1)!=24$ different $E(t)$ with two polarities each, of which 12 are non-identical with respect to the time axis inversion (FIGS. 4a-4l). Any of them provides ion separations by coefficient d, with $E_C$ given by equation [21]:

$$E_C=[(d/N^8)E_D^9/256+\overline{o}(eE_D^{11}/N^{10})]/\Delta t \quad [21]$$

with the leading term coefficient equal to $1/4$ of $1/64$ in equation [19], following the rule postulated above. These waveforms also produce ion trajectories with different $\Delta r$ ($C_E \approx 0.209$, $C_E \approx 0.282$, or $C_E \approx 0.320$) and so again yield a different instrumental response.

The present optimization approach involves $(n-1)$ variables, so maximizing $\int E^{2n-1}(t)dt$ is a growing challenge at higher n. Still, the procedure conceptually allows designing $E(t)$ to cancel any finite number of the leading terms in equation [3], thus enabling separations of arbitrarily higher order.

Below we disclose the major considerations associated with practical HODIMS implementation. Separations in HODIMS can be effected, e.g., by the filtering mechanism, wherein ions are injected in the gap between two electrodes that carry voltage waveforms generating the desired time-dependent electric field in-between, and species with unbalanced trajectories are removed by neutralization on electrode(s). Again, ions can be pushed through the gap by either a gas flow or a longitudinal electric field component perpendicular to the periodic time-dependent electric field. That longitudinal component may be created, e.g., by a DC potential gradient along segmented electrode(s) that may be constant or have an arbitrary gradient. Hence HODIMS can utilize all electrode geometries known for FAIMS, including planar, cylindrical, and spherical, and also the cylindrical configuration with a hemispherical terminus implemented, e.g., in a commercial Selectra instrument (Ionalytics Corp., Ottawa, Ontario, Canada).

With a planar gap, any voltage waveform produces a spatially homogeneous electric field (i.e., of equal direction and magnitude in all points), except for fringe effects. The field becomes inhomogeneous in a curved gap, increasing toward the electrode surface of higher curvature. In cylindrical and spherical geometries (with the proper field polarity), this would cause focusing that keeps ions near the gap median (counteracting diffusion and Coulomb repulsion), which greatly improves sensitivity and permits effective ion trapping at high pressures. As follows from equations [11], [16], [19], and [21], the effect becomes stronger with increasing n as the dependence of $E_C$ on $E_D$ gets steeper. Thus HODIMS could be performed in cylindrical geometries where ion focusing is critical, and would enable the operation of atmospheric-pressure ion guides and traps. Because of more effective ion focusing and confinement at higher n, the ion transmission efficiencies and saturation ion currents of HODIMS analyzers and guides and charge capacities of HODIMS traps may significantly exceed the same parameters for FAIMS analyzers and traps.

The temperature of at least one electrode may be controlled by temperature control devices that effect either heating or cooling to a desired temperature. As known in the art, such devices may provide adjustable or programmable temperature control with high precision achieved using, e.g., thermocouples and feedback loops. In particular, temperatures of at least two of the electrodes disposed on the different sides of analytical gap may differ providing a temperature gradient across the analytical gap. That results in the gradient of N and thus of E/N across the gap, creating a pseudopotential well inside the gap. This well may likewise be used to guide or trap ions within the analytical gap, alone or in conjunction with the well created by inhomogeneous electric fields in curved gap geometries, as disclosed above.

Choice of Asymmetric Waveform

As derived above, for $n \geq 4$ some of the optimum E(t) result in ion trajectories with different $\Delta r$. A smaller $\Delta r$ value allows a narrower analytical gap for any given electrode geometry (e.g., planar, cylindrical, or spherical) and thus proportionately lower voltages for the same E(t) profile. The electrical engineering task is always simplified by minimizing rf voltages, hence in general E(t) yielding minimum $\Delta r$ are preferred, although not limited thereto. In particular, those are the E(t) shown in FIGS. 3a and 3b for n=4 ($C_E \approx 0.257$) and FIGS. 4b, 4e, 4f, and 4h for n=5 ($C_E \approx 0.209$). Other hardware considerations, such as finite switching speed, may favor E(t) with the smallest change between any consecutive voltage settings ($\Delta E$). The optimum E(t) have fixed $\Delta E$ for n=2 and 3, but not for higher n. For n=4, waveforms in FIGS. 3e-3f involve $\Delta E \approx 1.22 E_D$ vs. $\approx 1.90 E_D$ for those in FIGS. 3a-3d. For n=5, the lowest $\Delta E \approx 1.27 E_D$ is for FIG. 4l vs. $\approx 1.50 E_D$ for FIG. 4c $\approx 1.73 E_D$ for FIGS. 4a, 4d, 4e, 4g, and $\approx 1.94 E_D$ for FIGS. 4b, 4f, 4h-4k. However, for either n=4 or n=5, none of the E(t) that minimize $\Delta r$ has the lowest $\Delta E$ and vice versa. Reducing the cumulative voltage change, $\Delta E_{tot}$, per period (and thus the average electrical current in the system) may also be important, for example because of power consumption or heat dissipation limitations. The waveforms for $n \geq 4$ have significantly different $\Delta E_{tot}$: $\approx 3.80 E_D$ (FIGS. 4c-4f) and $\approx 5.49 E_D$ (FIGS. 4a-4b) for n=4; $\approx 3.88 E_D$ (FIGS. 4c, 4g, 4j, 4l), $\approx 5.07 E_D$ (FIGS. 4d, 4i), $\approx 5.23 E_D$ (FIGS. 4a, 4k), and $\approx 6.42 E_D$ (FIGS. 4b, 4e, 4f, 4h) for n=5. As seen here, the lowest $\Delta E_{tot}$ is compatible with the lowest $\Delta E$, pointing to options (FIGS. 3e and 3f) for n=4 and (FIG. 4l) for n=5 as perhaps the most amenable to electrical engineering. However, minimization of $\Delta E_{tot}$ is inconsistent with that of $\Delta r$, and the latter may take priority.

Table 1 lists characteristic parameters of optimum asymmetric waveforms for FAIMS and HODIMS up to the 5th order.

TABLE 1

Characteristic parameters of optimum asymmetric waveforms for FAIMS and HODIMS up to the 5th order.

|  | $\Delta E/E_D$ | $\Delta E_t/E_D$ | $C_E$ |
|---|---|---|---|
| FAIMS | 1.5 | 3 | 0.333 |
| HODIMS, n = 3 | 1.81 | 3.62 | 0.324 |
| HODIMS, n = 4 | 1.22-1.90 | 3.80-5.49 | 0.257-0.321 |
| HODIMS, n = 5 | 1.27-1.94 | 3.88-6.42 | 0.209-0.320 |

Overall magnitudes of $\Delta E$ and $\Delta E_{tot}$ for HODIMS of $3^{rd}$-$5^{th}$ orders are close to those for FAIMS, indicating a broadly similar difficulty of implementation in electrical circuitry. Further, each E(t) may have two polarities. As in FAIMS, polarities are interchangeable for a planar gap but not for curved geometries where ions focused with one polarity are defocused with the other. The proper polarity is set by combination of ion charge (positive or negative) and the sign of higher-order coefficient for chosen n (b, c, d, etc.), creating four operational modes: P1, P2, N1 and N2. Measurements indicate that both b>0 and b<0 are possible; the same should apply to coefficients c, d. Hence, all four modes would likely be encountered in HODIMS of any order. Signs of different coefficients in equation [3] are generally independent, e.g., ions with positive "a" may have "b" of either sign; and, ions with negative "b" may have "a" of either sign. Hence, changing n may necessitate switching waveform polarity.

Practical HODIMS embodiments could employ not the ideal E(t) but their approximations via combinations of harmonic waveforms. These E(t) forms are fundamentally suboptimum, but may prove easier or less expensive to implement in electrical hardware.

Intensity of Electric Field and Separation Power

By equation [3], (E/N) at which a term exceeds a given threshold tends to increase for each subsequent term. Thus higher separation orders require greater (E/N), and a steeper dependence of <v> on $E_D$ at higher n means an increasingly abrupt emergence of a significant effect. The strongest field allowable in any gas is limited by electrical breakdown, with the point of onset ($E_{BR}$) depending on the gas properties (identity and N), the gap width (g), and electrode geometry. For a practical g~0.5-2 mm, $E_{BR}/N$ (for $N_2$ or air at STP conditions) ranges from $\approx 220$ to $\approx 160$ Td. So for practical separations the HODIMS effect must be large enough at realistic electric field intensities. The increase of required $E_D$ at higher n will preclude useful HODIMS operation beyond a certain n. However, absolutely no limitation of the scope of this invention with regard to HODIMS order to be implemented or field intensity to be used is hereby intended.

Figure 5:
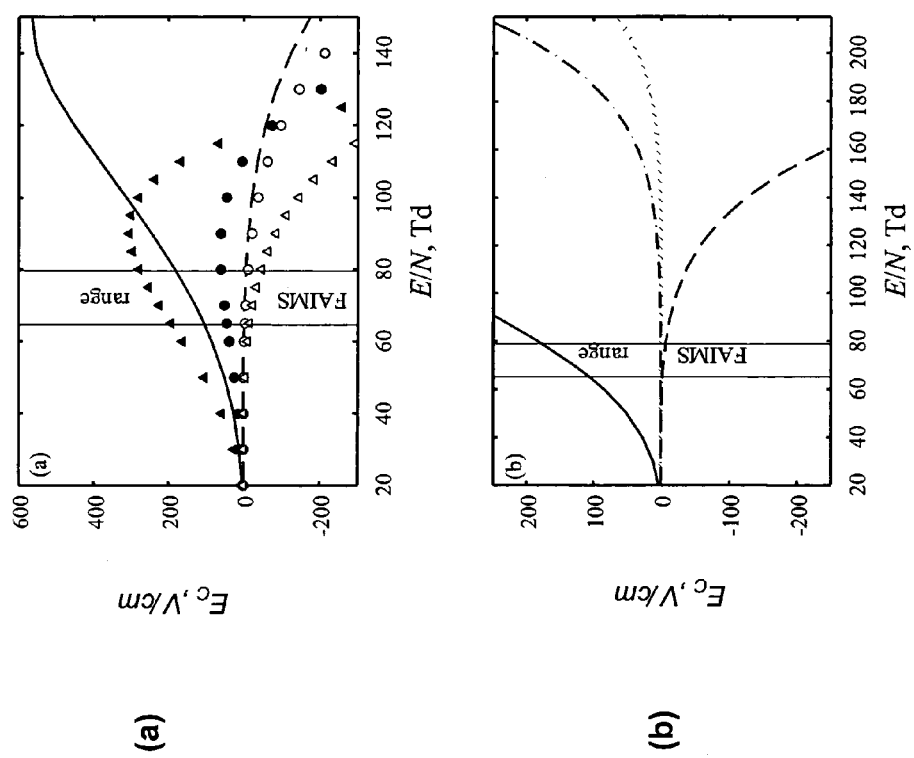
FIG. 5 present estimates for compensation field as a function of dispersion field for differential ion mobility separations with n=2-5. Lines are for a hypothetical "average" amino acid, for separation orders of n=2 (solid), n=3 (dashed), n=4 (dash-dot), and n=5 (dotted). In (a), filled symbols are for n=2 and empty ones are for n=3: circles for $H^+$Lysine and triangles for an "average" ketone.

In a given experiment, the $E_D$ needed to effect separation depends on the magnitude of coefficients in equation [3] with the chosen n. Information about typical values of those coefficients is scarce for "b" and currently non-existent for higher-order terms. Compilations of known b come principally from FAIMS data for protonated and deprotonated ions of 17 amino acids in air, where b (in $10^{-10}$ Td$^{-4}$) values range from $-5.95$ to $0.79$ with a mean absolute value of 1.47 and a median value of 1.34. In the same set, a values (in $10^{-6}$ Td$^{-2}$) range from 1.27 to 17.4 with a mean of 6.78 and a median of 6.00. The similarity of mean and median values in both sets suggests a representative selection of a and b. These data allow estimating $E_D/N$ that, for n=3, provides $E_C$ (and thus the resolving power) comparable to those in FAIMS at typical $E_D$ as illustrated in FIG. 5a. In FAIMS using the ideal E(t) of equation [9], a hypothetical ion with mean {a; b} would have $E_C$=100-180 V/cm at $E_D/N$=65-80 Td. In $3^{rd}$-order separations, $E_C$ would reach the same magnitude at $E_D/N$=130-150 Td, which is below the electrical breakdown threshold even in the worst case of g=2 mm. The |b|/|a| ratio for many ions in the set exceeds $2.2 \times 10^{-5}$ Td$^{-2}$ in the average scenario above, and a comparable $E_C$ would be obtained at lower $E_D$. For example, H$^+$Lysine with a=3.83 and b=-2.51 (and thus |b|/|a|=$6.6 \times 10^{-5}$ Td$^{-2}$) has a lower $E_C$=45-60 V/cm at $E_D/N$=65-80 Td in FAIMS. Achieving equal $E_C$ in $3^{rd}$ order HODIMS would call for $E_D/N$=100-110 Td as illustrated in FIG. 5a. FAIMS becomes useful (though suboptimum) at $E_D/N \approx 40$-50 Td, thus, fields needed for a comparable HODIMS performance can be estimated. For example, as illustrated in FIG. 5a, fields at $E_D/N \approx 100$-115 Td are useful for "average" amino acids, and $E_D/N \approx 90$-105 Td for H$^+$Lysine.

Some ions have low |b| that would not yield a significant $E_C$ at any $E_D/N$ up to the breakdown threshold. However, such a condition is not specific to higher-order separations but inherent in differential IMS in general. The a and b in the above set are for $E/N \leq 65$ Td should not be simply extrapolated to higher fields, as the aim is not to predict separation parameters for particular species, but to disclose the electric field strength needed for HODIMS in general.

All preceding estimates are broadly consistent with those derived from the two other published (less extensive) sets of b coefficients for protonated ketones and for protonated organophosphorus compounds. Mean absolute values for "a" and "b" in those sets are: {16.0; −9.26} and {3.94; −8.18}, respectively, for 8 ketone monomers and 8 dimers; {2.57; −1.06} and {0.58; −0.73}, respectively, for 10 organophosphorus monomers and 7 dimers. Thus the mean |b| for organophosphorus ions is similar to that for amino acids, while that for ketones is nearly an order of magnitude higher. In the result, the $3^{rd}$ order HODIMS of typical ketones would become operational already at $E_D/N \sim 70$-$80$ Td and broadly as effective as FAIMS at ~105-115 Td (see FIG. 5a).

The values for coefficients (c, d, and further) controlling HODIMS for $n \geq 4$ are unknown, but could be crudely estimated by noting that, in expansions describing physical phenomena such as equation [3], ratios of coefficients for consecutive terms often have the same order of magnitude. Indeed, for amino acid data described previously herein, ratios of the mean coefficients with the $2^{nd}$ and $1^{st}$ terms of equation [3] (i.e. the mean |a|) is $6.8 \times 10^{-6}$ Td$^{-2}$ and the same ratio for $3^{rd}$ and $2^{nd}$ terms is, as stated, $2.2 \times 10^{-5}$ Td$^{-2}$. Hence, as a first approximation, the expression [22]

$$|d|/|c| = |c|/|b| = |b|/|a| \qquad [22]$$

yields a mean value for $|c| = 3.2 \times 10^{-15}$ Td$^{-6}$, and a mean value for $|d| = 6.9 \times 10^{-20}$ Td$^{-8}$. These values allow projection of typical separation parameters for $4^{th}$ and $5^{th}$ order HODIMS for amino acid ions (see FIG. 5b). In this scenario, a useful operation would be achieved at $E_D/N \approx 150$-$170$ Td for n=4 and ≈190-210 Td for n=5. For typical gap widths, these ranges are slightly below the breakdown thresholds for n=4 and right at them for n=5. However, values for coefficients c or d for many ions may exceed exemplary values stated hereinabove, resulting in substantial HODIMS effects for n=4 and n=5 at lower dispersion fields. For instance, the mean |b|/|a| ratio in the ketone set is $5.8 \times 10^{-5}$. Equation [22] yields mean $|c| = 54 \times 10^{-15}$ Td$^{-6}$ and a $|d| = 310 \times 10^{-20}$ Td$^{-8}$. At these values for |c| and |d|, useful separations would require $E_D/N$ 100-115 Td for n=4 and 125-135 Td for n=5, well short of the electrical breakdown thresholds for operable gap widths.

All comparisons vs. FAIMS made hereinabove are for ideal rectangular E(t) which is more effective than practical sinusoid-based waveforms by ~40-50%. Thus, HODIMS of the present invention embodied using the ideal E(t) would be more effective by the same ~40-50% if benchmarked vs. commercial FAIMS. As noted herein, actual HODIMS waveforms will not be optimum in comparison to the ideal E(t).

Higher-order separations can also be effected using gas buffers other than $N_2$ or air at 1 atm, some of which are significantly more resistant to electrical breakdown. For example, a gap of 0.5-2 mm filled with $SF_6$ (a standard gas insulator for high-voltage components) supports $E/N \approx 380$-$410$ Td, and yet higher E/N are accessible using electronegative gases based on halogenated carbons. While FAIMS in $SF_6$ has been reported, the values of b, c, d . . . in K(E) expansion are not known for any ion. However, values for a of representative ions in $SF_6$ are close to those in $N_2$ and $O_2$, and there is no reason for higher-order coefficients to be abnormally low. Accordingly, the ability to raise $E_D/N$ to ~400 Td should allow useful separations up to n=5, and perhaps for yet higher orders. When operation in pure $SF_6$ or similar insulators is impractical, even a small admixture of those gases to the buffer (such as $N_2$) raises the breakdown threshold disproportionately to the fraction of insulating gas. For example, the threshold for a 90:10 mixture of $N_2$:$SF_6$ is ~150% of that for pure $N_2$. In addition, a gas mixture may be selected having a composition that, at sufficiently high electric field, yields a substantial deviation from Blanc's law for ion mobilities. These deviations may increase the resolution, specificity, and peak capacity of HODIMS analyses, and/or improve sensitivity by augmenting the ion focusing in a pseudopotential well inside the analytical gap.

Gap Width and Waveform Frequency

The optimum gap width in differential IMS is determined by $\Delta r$ for ions of interest. A g value smaller than or close to $\Delta r$ causes a rapid indiscriminate elimination of ions, whereas a gap that is too wide can pass significantly unbalanced ions resulting in poor separation quality. By equation [17], $\Delta r$ is proportional to $C_E$ and $E_D$, and both parameters depend on n as discussed above. However, the decrease of optimum $C_E$ and increase of required $E_D$ with increasing n partly offset each other. For example, choosing the lowest $C_E$ possible for a given n (Table 1) and reasonable $E_D/N$ values of 80, 130, 160, and 200 Td for n=2-5, respectively, yields ($C_E E_D/N$) quantities of 26.7, 42.1, 41.1, and 41.8 Td. Thus HODIMS for all n considered would involve approximately equal $\Delta r$ values that differ from typical FAIMS values by a factor of ~1.5 only. This indicates that separations of all higher orders may be implemented using one gap width. Other factors being equal, a gap somewhat wider than that employed in FAIMS can be used, with the waveform voltage increased proportionately to establish the same $E_D$. The alternative is to increase the E(t) frequency in proportion to ($C_E E_D/N$) to produce constant $\Delta r$ by equation [17]. Estimates suggest that HODIMS can be operated using mechanical hardware similar to that for FAIMS, enabling a rapid switching between all n that can be effected at the software level by changing only the waveform profile and adjusting the amplitude and/or the frequency.

Utility of Higher-Order Separations

As discussed herein, FAIMS and MS tend to be more orthogonal than IMS and MS. There also is a significant orthogonality between FAIMS and IMS dimensions, which enables 2-D separations by FAIMS/IMS. However, FAIMS is still substantially correlated to MS. For example, in FAIMS in $N_2$ or air buffer, ions with masses up to several hundred Da (including monatomics, amino acid ions, and other simple organic ions) are "A-type" (i.e., have a positive coefficient a), while large ions (including all peptides) are "C-type" (i.e., have a negative coefficient a). The inverse correlation between "a" and m is also found within many homologous series, e.g., for the previously described sets of ketone and organophosphorus compounds, and amino acid ions. Classification of ions by types depends on the gas: an "A" ion in one buffer (e.g., Cs$^+$ in $N_2$ or $O_2$) may become "C" in another (e.g., Cs$^+$ in He). Yet, the trend of a decreasing with increasing ion mass remains, in agreement with fundamental dynamics of ion-molecule collisions.

Figure 6:
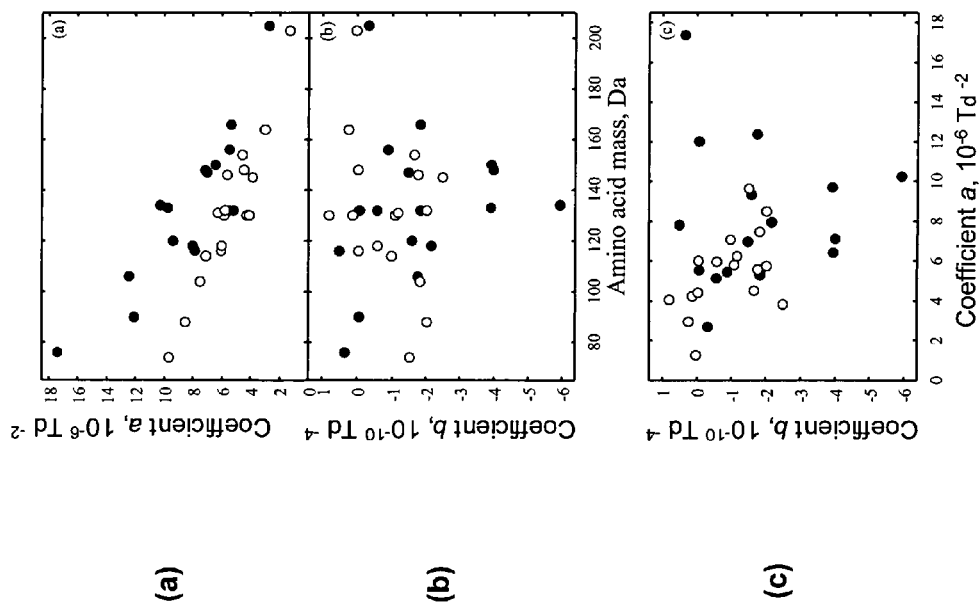
FIGS. 6a-6c illustrate orthogonality between separation dimensions of FAIMS and MS (FIG. 6a), $3^{rd}$-order differential ion mobility separations and MS (FIG. 6b), and $3^{rd}$-order differential ion mobility separations and FAIMS (FIG. 6c) for amino acid cations (empty circles) and anions (filled circles).

The orthogonality between higher order separations and MS (or IMS) should increase with increasing n, for the same reason why MS is generally more orthogonal to FAIMS than to IMS. Measurements for both amino acid cations and anions support this conjecture (see FIGS. 6a-6c). All ions in these experiments are singly charged, so m/z=m. The values for coefficient a are clearly related to mass, with a linear correlation ($r^2$) of 0.87 for (+) and 0.71 for (−) ions (FIG. 6a). In contrast, values of coefficient b are entirely independent of m, with $r^2$ of 0.09 for (+) ions and 0.04 for (−) ions (FIG. 6b). Similarly, values of b are independent of a, with $r^2$ of 0.25 for (+) ions and 0.00 for (−) ions (FIG. 6c). This means that $3^{rd}$-order separations of an amino acid mixture would be completely orthogonal to both FAIMS and MS dimensions. Since IMS and MS for ions of any specific charge state are strongly correlated, $3^{rd}$-order HODIMS would be orthogonal to IMS, too. From first principles, HODIMS for $n \geq 4$ should be at least as orthogonal to MS, IMS, and FAIMS as that for n=3.

The orthogonality expected between HODIMS and MS would make HODIMS/MS a powerful analytical method, especially for applications focused on the characterization of isomeric and isobaric ions. Both IMS/MS and FAIMS/MS are employed for this purpose, but limited orthogonality between the two dimensions involved generally results in relatively low 2-D separation peak capacities, which impedes analyses of complex mixtures. As illustrated in FIGS. 6a-6c, the HODIMS/MS combination is expected to largely avoid these problems, making HODIMS preferable to IMS or FAIMS, even at inferior resolution of HODIMS. For example, K(0) of $H^+$Leucine and $H^+$Isoleucine in $N_2$ differ by ~1% (1.618 and 1.632 $cm^2/(Vs)$, respectively), which barely allows distinguishing these isomers in high-resolution IMS. The difference between coefficients a (respectively 4.24 and 4.06) is greater at 4%, but is just sufficient for high-resolution FAIMS analyses. Similarly for negative ions, a for (Leucine—H)$^-$ and (Isoleucine—H)$^-$ differ by ~5% (respectively 5.43 and 5.15), which is just enough for FAIMS separation. In comparison, the values of b differ by ~560% (0.12 vs. 0.79) for cations and ~220% (−1.85 vs. −0.58) for anions. Differences of that magnitude should allow a complete separation even with a rudimentary resolving power. More accurately, the difference between separation parameters of two species should be compared to the width of separation space. For amino acid cations, that width equals 8.38 in a dimension and 3.30 in b dimension. Hence the peak capacities needed to distinguish $H^+$Leucine from $H^+$Isoleucine are 8.38/(4.24−4.06)=47 in FAIMS and 3.30/(0.79−0.12)=4.9 in HODIMS for n=3. Similarly for anions, the separation space width is 14.7 for a and 6.45 for b, and the peak capacities needed are 52 in FAIMS but only 4.8 in HODIMS for n=3. In other words, HODIMS could possibly provide the peak capacity an order of magnitude higher than FAIMS at equal resolution, or equal to FAIMS at ~1/10 of resolution. This means that HODIMS can operate potentially at roughly half the dispersion fields projected in the preceding section based on FAIMS resolution benchmarks, which would place required $E_D/N$ for all $n \leq 5$ in the easily accessible range of <110 Td.

HODIMS may analyze ions generated by any source, including electrospray ionization, desorption electrospray ionization, thermospray, sonic spray, matrix-assisted laser desorption ionization, atmospheric pressure matrix-assisted laser desorption ionization, surface-enhanced laser desorption ionization, laser vaporization, laser desorption, secondary ion ionization, photoionization, atmospheric pressure photo-ionization, arc discharge, coronary or cathode discharge, electron impact, chemical ionization, atmospheric pressure chemical ionization, liquid evaporation, liquid clustering, "pick-up", and combinations thereof.

Ions of interest may be introduced into the HODIMS analytical gap continuously or in discrete pulses, e.g. using a mechanical shutter and/or electric gating at the entrance to HODIMS stage. The gas pressure in the gap may exceed the pressure in a preceding region from which the ions enter the gap, such that the gas flows out of the gap in the direction opposite to that of ion ingress. The time of ion passage through the gap may be monitored, and, when ions are moved through the gap by secondary electric field, a separation or characterization (identification) of ions by IMS may be effected simultaneously with HODIMS filtering.

HODIMS can be usefully coupled to either or both IMS and FAIMS to enable 2-D and 3-D gas-phase separations, with or without MS analyses. Separations in further dimensions can, in principle, be achieved by stacking HODIMS filters operated at different n. Further, HODIMS can also be interfaced with condensed-phase separations such as reverse-phase and/or strong cation exchange liquid chromatography in front of ion source. HODIMS can in addition be sequentially coupled on-line or off-line with other analytical techniques including but not limited to mass spectrometry (MS) including tandem MS and multiple MS stages of any kind, gas chromatography (GC), photoelectron spectroscopy, photodissociation spectroscopy, liquid chromatography (LC) including, but not limited to, normal phase LC, reversed phase LC, and strong-cation exchange LC, supercritical fluid chromatography, capillary electrophoresis, capillary isoelectric focusing, and gel separations in one or more dimensions (including SDS-PAGE and 2-D gel).

A portion of the ions in the gas phase may be further dissociated during, at the end of, or after the separation, by techniques including, but not limited to, collisional dissociation, thermal dissociation, field dissociation, photodissociation, electron capture dissociation, and combinations thereof. This may be used in multidimensional separations to increase the orthogonality of between HODIMS and other stages, thereby increasing the overall peak capacity and specificity of analyses.

Electrical Hardware Embodiments

The asymmetric waveforms needed for HODIMS operation may be generated using a variety of electrical hardware and devices. An exemplary system 100 for that purpose will now be described with reference to FIGS. 7a, 7b, and 8.

Figure 7:
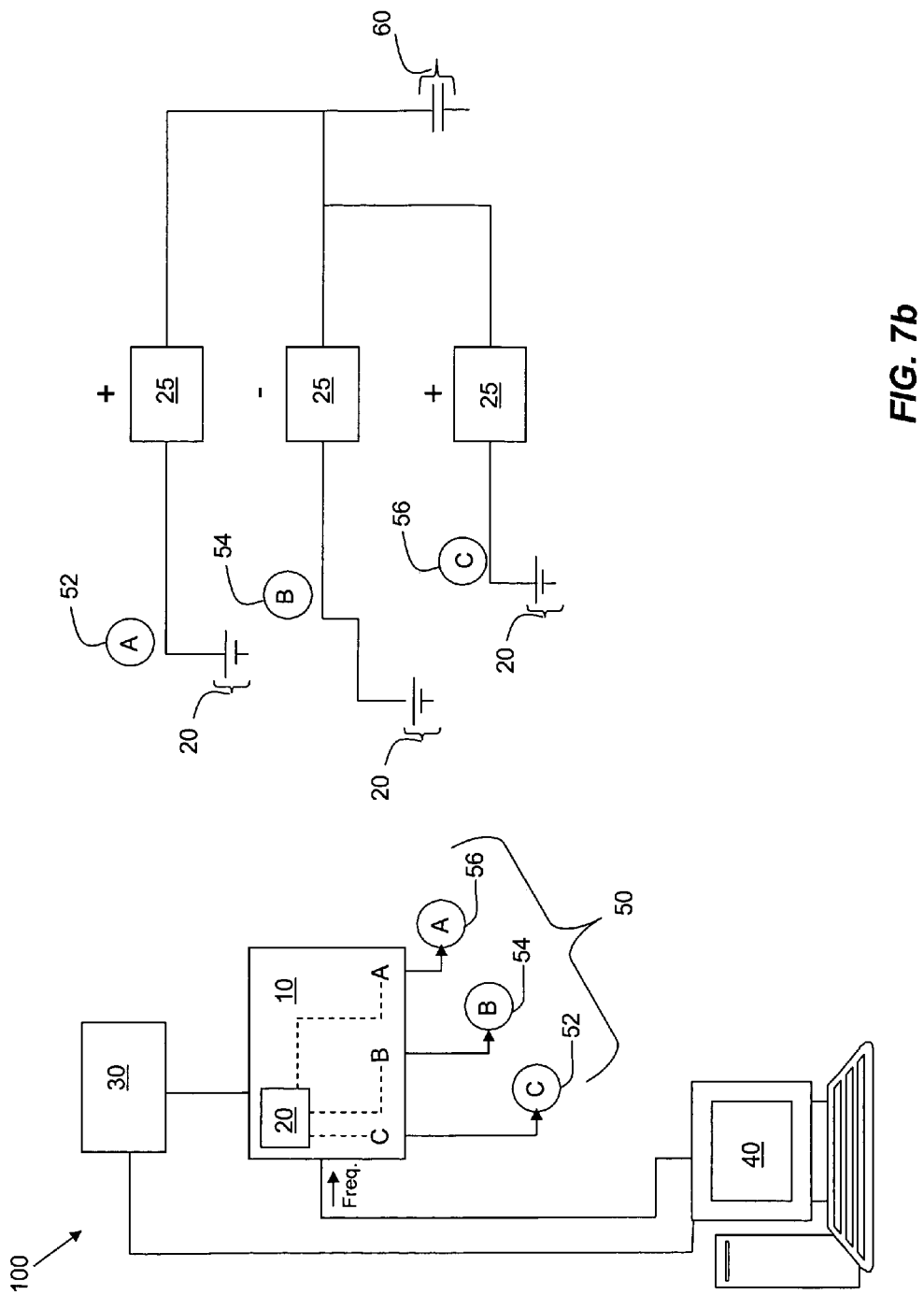
FIG. 7a illustrates a system for generating series of high voltage pulses, according to an embodiment of the invention.
FIG. 7b illustrates a tuned circuit for generating periodic waveform components, according to an embodiment of the invention.

FIG. 7a illustrates a system 100 configured to output periodic asymmetric waveforms, described previously herein, according to an embodiment of the invention. System 100 comprises a waveform (sequence or signal) generator 10 (e.g., a 200 MS/s, 16-bit waveform generator, National Instruments Corp., Austin, Tex.) coupled electrically to a power supply 30 interfaced to a controller 40 (e.g., computer) providing suitable frequency adjustment/generation and timing inputs for waveform generator 10. Generator 10 may comprise any number of oscillating circuits 50 including, e.g., LC circuits, but is not limited thereto. In one illustrative configuration, generator 10 comprises, e.g., three circuits 50 as illustrated in FIG. 7b, i.e., circuit A 52, circuit B 54, and circuit C 56, each circuit 50 outputting a generally periodic waveform. Waveforms are superposed to produce a time-dependent (positive or negative) voltage with the desired E(t) profile applied across electrodes 60 of any geometry of a HODIMS device 100. Generator 10 may further comprise one or more adjustable (e.g., programmable and/or switched) power source(s) 20 each comprising at least one solid state switch 25 in a series configuration coupled electrically to power supply 30. Switches 25 include, but are not limited to, e.g., high-voltage MOSFETs, switching networks, transistors, and the like, or combinations thereof. Power sources 20 may further comprise computer-controlled power supplies 30. No limitations are intended. Sequencing of pulses will now be described with reference to FIG. 8.

Figure 8:
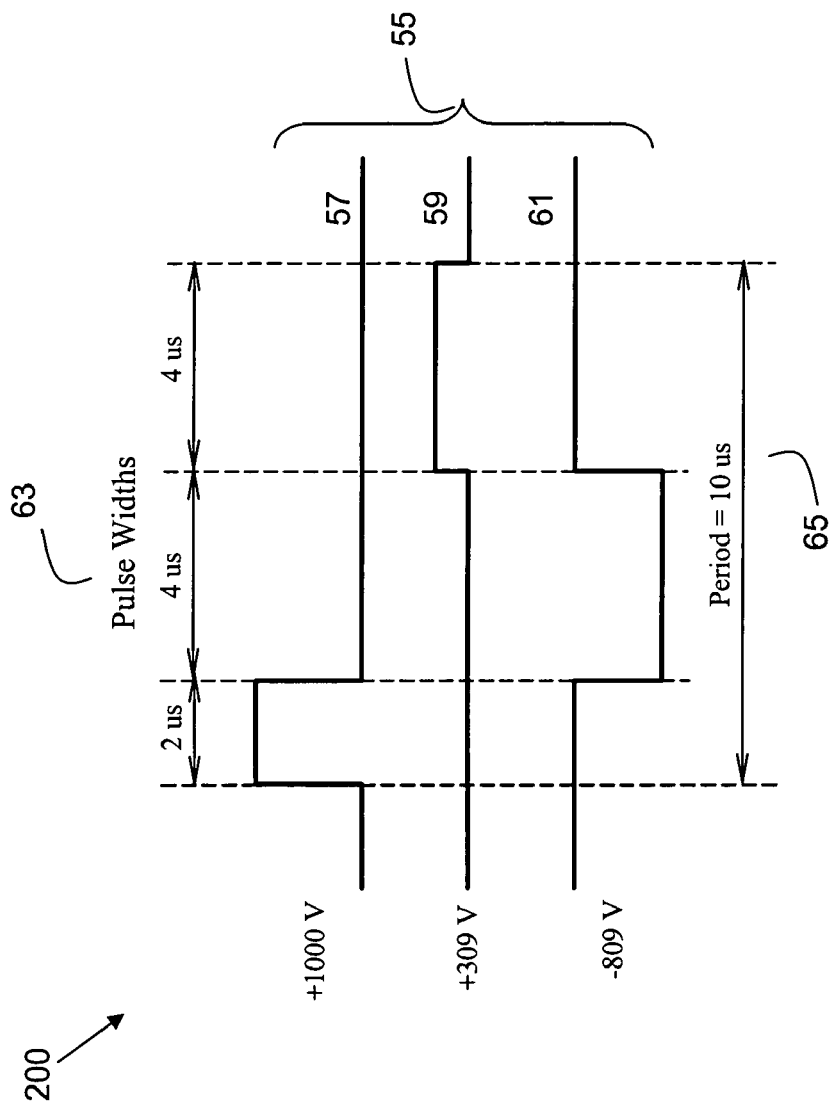
FIG. 8 illustrates a typical pulse sequence generated by the apparatus of the invention.

FIG. 8 illustrates the generation of the specific E(t) presented in FIG. 2b. A waveform having an exemplary 100 kHz frequency is derived from individual, superposed pulses 55 with the defined sequence 200. A first (+) pulse 57 generated by a first power source 20 or supply 30 has amplitude of +1,000 V and a pulse width (duration) 63 of 2 µs. A second (+) pulse 59 generated by a second power source 20 or supply 30 has amplitude of +309 V and duration 63 of 4 µs. A third (−) pulse 61 generated by a third power source 20 or supply 30 has amplitude of −809 V and duration 63 of 4 µs. Superposition of individual pulses 57, 59, and 61 of sequence 200 yields a complex waveform as illustrated in FIG. 2b with peak-to-peak amplitude of 1,809 V and period 65 of 10 µs. Each pulse 55 in the defined sequence 200 actively drives voltage achieved at the end of a preceding pulse 55 minimizing RC voltage decay in the associated waveform thereby providing near-ideal E(t) necessary for ion separations.

In a further embodiment, at least one pulse 55 or voltage is applied to one of electrodes 60 of a HODIMS analyzer or device and other pulses 55 or voltages are applied to other electrodes 60 such that voltage across the analytical gap has a time-dependent profile of desired E(t), even if the voltage on each electrode 60 individually does not have that profile. Each power source 20 may be configured to provide at least one of the distinct voltages composing E(t). All configurations as will be envisioned by those of skill in the art are encompassed hereby. No limitations are intended.

As will be understood by those of skill in the art, waveform amplitudes are fully adjustable. For example, generator 10 may be coupled to transformers and/or other components or devices, whereby generator 10 provides a sub-scale form of E(t) with, e.g., the transformer amplifying the sub-scale form to a desired $E_D$ amplitude. All pulse sequencing, voltages, pulse widths, pulse periods and associated devices as will be contemplated by those of skill in the art are encompassed herein without limitation.

This application has addressed the essential elements that determine the feasibility and utility of the present invention for higher-order differential ion mobility separations, including the criteria for optimum hardware design and instrumental operation. As will be recognized by those of skill in the art, molecular dynamics simulations of FAIMS analyzers can be expanded to new waveforms involved in HODIMS. In addition, a comprehensive treatment of HODIMS separations may further include, e.g., an accurate modeling of resolution, ion transmission efficiency, and ion focusing and trapping that will guide the hardware development and choice of operational parameters. However, no limitations are hereby intended. For example, successful realization of HODIMS may depend on approximating the ideal waveforms by superposed harmonic oscillations in a way that judiciously balances the operational efficiency and engineering complexity. Hence the representation of ideal E(t) in harmonic oscillations may need to be optimized in simulations, as will be recognized by those of skill in the art. Further, it will be recognized that non-Blanc effects that control and often substantially benefit AIMS in gas mixtures will also be manifested in HODIMS. As commonly happens with nonlinear phenomena, such effects can become more pronounced with increasing separation order. Thus, methods involving heteromolecular buffer gases or addition of volatile vapors to the buffer gas can be employed in conjunction with the present invention.

We claim:

1. An ion mobility method for separation, characterization, or identification of ions, comprising the steps:
    introducing said ions into an analytical gap filled with a gas;
    establishing a periodic time-dependent electric field of intensity E over said analytical gap, said periodic time-dependent electric field cancels contributions to time-averaged ion motion of a number, n (where n≧2), of leading terms in a series expansion for ion mobility, K, as a function of E/N (where N is number density of said gas), via a polynomial in powers of E/N:

$$K(E/N)=K(0)[1+a(E/N)^2+b(E/N)^4+c(E/N)^6+d(E/N)^8+\ldots a_j(E/N)^{2j}];$$

thereby achieving separation, characterization, or identification of said ions based substantially on coefficients with the $(n+1)^{th}$ and subsequent terms of said series expansion: $a_j$ where j=n−1.

2. The method of claim 1, wherein said analytical gap is contained between at least two electrodes, and said electric field is produced by at least one voltage waveform applied to at least one of the electrodes.

3. The method of claim 2, wherein said electric field is a superposition of electric fields produced by voltage waveforms applied to at least two electrodes.

4. The method of claim 2, wherein said electrodes have a planar geometry.

5. The method of claim 4, where said electrodes are parallel, thereby establishing a spatially homogeneous electric field.

6. The method of claim 2, wherein at least one of said electrodes has a curved geometry, thereby establishing a spatially inhomogeneous electric field.

7. The method of claim 6, wherein said geometry is selected from the group of cylindrical, conical, spherical, hemispherical, ellipsoidal, ovoid, and combinations thereof.

8. The method of claim 6, wherein said electrodes have the geometry selected from the group of two coaxial cylinders, two concentric spheres or hemispheres, and combinations thereof.

9. The method of claim 6, further comprising selecting a field polarity such that said inhomogeneous electric field creates a pseudopotential well inside said analytical gap, thereby focusing or confining a plurality of ions within said gap.

10. The method of claim 9, wherein said confining is employed to guide said plurality of ions through said analytical gap to a desired volume in space, trapping said plurality of ions by containment in said well, temporarily storing said plurality of ions by containment in said well, or combinations thereof.

11. The method of claim 2, further comprising controlling the temperature of at least one of said electrodes.

12. The method of claim 11, wherein the temperatures of at least two of the electrodes differ, thereby providing a temperature gradient across the analytical gap that renders the value of E/N across said analytical gap spatially inhomogeneous, thereby creating a pseudopotential well inside said gap that focuses or confines a plurality of ions within said gap.

13. The method of claim 12, wherein said confining is employed to guide said plurality of ions through said analytical gap to a desired volume in space, trapping said plurality of ions by containment in said well, temporarily storing said plurality of ions by containment in said well, or combinations thereof.

14. The method of claim 1, wherein ions are moved through said analytical gap by a gas flow, a secondary electric field component perpendicular to said periodic time-dependent electric field, or combinations thereof.

15. The method of claim 14, wherein said secondary electric field is produced using at least one segmented electrode carrying a voltage gradient.

16. The method of claim 14, wherein said gas flow is heated or cooled before entering said analytical gap.

17. The method of claim 1, wherein said electric field is a superposition of elements selected from the group consisting of different discrete field settings applied over finite time intervals, different harmonic waveforms, and combinations thereof.

18. The method of claim 17, comprising (n+1) elements.

19. The method of claim 1, wherein said gas comprises a mixture of at least two homomolecular gases or vapors.

20. The method of claim 19, wherein said mixture has a composition resulting in a measurable deviation from Blanc's law for ion mobilities.

21. The method of claim 1, wherein said gas comprises a gas-phase insulator with high electrical breakdown threshold.

22. The method of claim 1, wherein said ions are introduced into said analytical gap continuously.

23. The method of claim 1, wherein said ions are injected into said analytical gap in discrete pulses.

24. The method of claim 1, wherein said ions are received directly or through others stages from a source selected from the group consisting of electrospray ionization, desorption electrospray ionization, thermospray, sonic spray, matrix-assisted laser desorption ionization, atmospheric pressure matrix-assisted laser desorption ionization, surface-enhanced laser desorption ionization, laser vaporization, laser desorption, secondary ion ionization, photoionization, atmospheric pressure photo-ionization, arc discharge, coronary or cathode discharge, electron impact, chemical ionization, atmospheric pressure chemical ionization, liquid evaporation, liquid clustering, "pick-up", and combinations thereof.

25. The method of claim 1, wherein the pressure of said gas in said analytical gap exceeds the pressure in an adjacent region from which said ions enter said analytical gap, such that said gas flows out of said analytical gap in the direction opposite to that of ion ingress.

26. The method of claim 1, wherein at least a portion of said ions is dissociated during, at the end of, or after said separation or characterization, by a technique selected from the group consisting of collisional dissociation, thermal dissociation, field dissociation, photodissociation, electron capture dissociation, and combinations thereof.

27. The method of claim 1 sequentially coupled to one or more iterations of said method having different values for said parameter n.

28. The method of claim 1, sequentially coupled on-line or off-line to at least one additional analytical method selected from the group consisting of ion mobility spectrometry, field asymmetric waveform ion mobility spectrometry, mass spectrometry, gas chromatography, photoelectron spectroscopy, photodissociation spectroscopy, liquid chromatography, strong cation exchange, supercritical fluid chromatography, capillary electrophoresis, capillary isoelectric focusing, gel separations in one or more dimensions, and combinations thereof.

29. An ion mobility apparatus for separation, characterization, or identification of ions, comprising:

a plurality of electrodes operably connected to a waveform-generating device;

said electrodes and said waveform-generating device are configured to establish a periodic, time-dependent electric field of intensity F over an analytical gap filled with a gas;

said periodic, time-dependent electric field cancels contributions to time-averaged ion motion of a number, n (where n≧2), of leading terms in a series expansion for ion mobility, K, as a function of E/N (where N is number density of said gas), via a polynomial in powers Of E/N:

$K(E/N)=K(0)[1+a(E/N)^2+b(E/N)^4+c(E/N)^6+d(E/N)^8+\ldots a_j(E/N)^{2j}]$;

thereby achieving separation, characterization, or identification of said ions based substantially on coefficients with the $(n+1)^{th}$ and subsequent terms of said series expansion: $a_j$ where $j=n-1$.

30. The apparatus of claim 29, wherein said analytical gap is contained between at least two electrodes, and said electric field is produced by at least one voltage waveform applied to at least one of the electrodes.

31. The apparatus of claim 29, wherein said electric field is a superposition of electric fields produced by voltage waveforms applied to at least two of the electrodes.

32. The apparatus of claim 29, wherein said electrodes have a planar geometry.

33. The apparatus of claim 32, where said electrodes are parallel, thereby establishing a spatially homogeneous electric field.

34. The apparatus of claim 29, wherein at least one of said electrodes has a curved geometry, thereby establishing a spatially inhomogeneous electric field.

35. The apparatus of claim 34, wherein said geometry is selected from the group of cylindrical, conical, spherical, hemispherical, ellipsoidal, ovoid, and combinations thereof.

36. The apparatus of claim 34, wherein said electrodes have the geometry selected from the group of two coaxial cylinders, two concentric spheres or hemispheres, and combinations thereof.

37. The apparatus of claim 29, further comprising at least one temperature-control device in thermal contact with at least one of said electrodes.

38. The apparatus of claim 29, wherein at least one of the electrodes is segmented with a voltage gradient thereon, thereby establishing a longitudinal electric field component perpendicular to said periodic, time-dependent electric field.

39. The apparatus of claim 29, further comprising a temperature-control device in thermal contact with said gas heating or cooling said gas prior to inflow into said analytical gap.

40. The apparatus of claim 29, operably connected, directly or through other stages, to an ion source selected from the group consisting of electrospray ionization, desorption electrospray ionization, thermospray, sonic spray, matrix-assisted laser desorption ionization, atmospheric pressure matrix-assisted laser desorption ionization, surface-enhanced laser desorption ionization, laser vaporization, laser desorption, secondary ion ionization, photoionization, atmospheric pressure photo-ionization, arc discharge, coronary or cathode discharge, electron impact, chemical ionization, atmospheric pressure chemical ionization, liquid evaporation, liquid clustering, "pick-up", and combinations thereof.

41. The apparatus of claim 29, sequentially coupled on-line or off-line to at least one additional analytical device selected from the group consisting of ion mobility spectrometers, field asymmetric waveform ion mobility spectrometers, mass spectrometers, gas chromatographs, photoelectron spectrometers, photodissociation spectrometers, liquid chromatographs, strong cation exchange units, supercritical fluid chromatographs, capillary electrophoresis units, capillary isoelectric focusing units, gel separation units, and combinations thereof.

42. The apparatus of claim 29, further comprising means for dissociating at least a portion of said ions during, at the end of, or after said separation.

43. The apparatus of claim 29, further comprising means for pulsing or gating ions at the entrance to said analytical gap, thereby allowing discrete ion packets inside said gap.

44. The apparatus of claim 29, wherein said waveform-generating device comprises a plurality of operably-connected oscillating circuits, each outputting a periodic waveform, wherein said waveforms are superposed to provide said periodic, time-dependent electric field.

45. The apparatus of claim 29, wherein said waveform-generating device comprises at least one switched power source.

46. The apparatus of claim 45, wherein said at least one switched power source comprises at least one solid state switch in a series configuration operably connected to a power supply.

47. The apparatus of claim 46, wherein said at least one switched power source comprises a computer-controlled power supply.

48. The apparatus of claim 47, wherein said computer-controlled power supply is operably connected to a sequence generator.

49. The apparatus of claim 45, wherein said at least one switched power source provides at least one of the distinct voltages composing a period of the time-dependent electric field.

50. The apparatus of claim 29, further comprising a transformer operably connected to the waveform-generating device, wherein the waveform-generating device generates a sub-scaled form of a periodic time-dependent voltage waveform and the transformer amplifies said sub-scaled form to a desired amplitude.

* * * * *